(12) United States Patent
Deng et al.

(10) Patent No.: US 11,760,660 B2
(45) Date of Patent: Sep. 19, 2023

(54) AUTOMATIC CONTROL SYSTEM AND METHOD FOR WATER TREATMENT OF THERMAL STERILIZATION KETTLE

(71) Applicant: Guizhou Education University, Guiyang (CN)

(72) Inventors: Mingsen Deng, Guiyang (CN); Hengxiu Yang, Guiyang (CN); Hujun Shen, Guiyang (CN); Xuefeng Zou, Guiyang (CN); Fushao Li, Guiyang (CN); Qingqing Wu, Guiyang (CN); Ling Chen, Guiyang (CN)

(73) Assignee: GUIZHOU EDUCATION UNIVERSITY, Guiyang (CN)

( * ) Notice: Subject to any disclaimer, the term of this patent is extended or adjusted under 35 U.S.C. 154(b) by 0 days.

(21) Appl. No.: 18/083,147

(22) Filed: Dec. 16, 2022

(65) Prior Publication Data
US 2023/0202868 A1 Jun. 29, 2023

(30) Foreign Application Priority Data
Dec. 29, 2021 (CN) .......................... 202111637815.7

(51) Int. Cl.
*C02F 1/00* (2023.01)
*G01N 21/85* (2006.01)
(Continued)

(52) U.S. Cl.
CPC ................ *C02F 1/008* (2013.01); *C02F 1/02* (2013.01); *C02F 1/50* (2013.01); *C02F 1/72* (2013.01);
(Continued)

(58) Field of Classification Search
None
See application file for complete search history.

(56) References Cited

U.S. PATENT DOCUMENTS

| | | | |
|---|---|---|---|
| 2007/0221552 A1* | 9/2007 | Denney ................. | B01D 21/30 210/85 |
| 2009/0152183 A1* | 6/2009 | Stewart .................... | A61L 2/04 165/279 |
| 2015/0191370 A1* | 7/2015 | Reedzt ................ | C02F 1/46109 210/243 |

FOREIGN PATENT DOCUMENTS

CN 112279326 A 1/2021

OTHER PUBLICATIONS

Theory and Practice of thermal sterilization of food, Chinalight Industry Press, 2014, pp. 1-6.
(Continued)

*Primary Examiner* — Richard C Gurtowski
(74) *Attorney, Agent, or Firm* — Owen G. Behrens; Smith & Hopen, P.A.

(57) ABSTRACT

The present disclosure relates to an automatic control system and method for water treatment of a thermal sterilization kettle. The system comprises a sampling module, a monitoring module and a control module, wherein the sampling module is used for respectively sampling hot water and cold water, and the monitoring module is arranged to respectively monitor online fluorescence signals in the sampled hot water and the sampled cold water; the control module is used for respectively controlling whether to add a compound medicament into a hot water area or not according to the online fluorescence signal of the sampled hot water and controlling whether to add the compound medicament into a cold water area or not according to the online fluorescence signal of the sampled cold water; and meanwhile, the monitoring module is further used for monitoring the residual chlorine signal of the sampled cold water.

20 Claims, 2 Drawing Sheets

(51) Int. Cl.
  *G01N 1/42* (2006.01)
  *C02F 1/02* (2023.01)
  *C02F 1/50* (2023.01)
  *C02F 1/72* (2023.01)
  *G01N 21/64* (2006.01)
  *G01N 21/84* (2006.01)

(52) U.S. Cl.
  CPC .............. *G01N 1/42* (2013.01); *G01N 21/64* (2013.01); *G01N 21/85* (2013.01); *C02F 2209/006* (2013.01); *C02F 2209/02* (2013.01); *C02F 2209/08* (2013.01); *C02F 2209/11* (2013.01); *C02F 2209/29* (2013.01); *C02F 2209/42* (2013.01); *C02F 2307/12* (2013.01); *G01N 2021/8416* (2013.01)

(56) References Cited

OTHER PUBLICATIONS

Office action for Application No. 202111637815.7, dated Aug. 10, 2022, pp. 1-12, English translation.
Chinese office action for Application No. 202111637815.7, dated Aug. 10, 2022, pp. 1-17.

\* cited by examiner

AUTOMATIC CONTROL SYSTEM AND METHOD FOR WATER TREATMENT OF THERMAL STERILIZATION KETTLE

CROSS-REFERENCE TO RELATED APPLICATION

This patent application claims the benefit and priority of Chinese Patent Application No. 202111637815.7, filed with the China National Intellectual Property Administration on Dec. 29, 2021, the disclosure of which is incorporated by reference herein in its entirety as part of the present application.

TECHNICAL FIELD

The present disclosure relates to the field of water treatment, in particular to an automatic control system and method for water treatment of a thermal sterilization kettle.

BACKGROUND

Canned and sealed (tinplate can, aluminum can, glass tube or soft package) food (such as canned food, drinks, meat and the like) needs to undergo sterilization before entering the market to reach the commercial sterility of food, so that the shelf life of food is prolonged. In industry, thermal sterilization is a main sterilization method. The canned and sealed food is sent to thermal sterilization equipment. Under high temperature conditions, various pathogenic bacteria and spoilage bacteria in the food can be killed by water or steam as a medium, so that the commercial sterility of food can be achieved.

There are many kinds of thermal sterilization equipment, and are classified in view of production continuity. There are two main types of thermal sterilization equipment, namely continuous sterilization kettles and discontinuous sterilization kettles. The continuous sterilization kettles typically comprise hydrostatic sterilization kettles and orbital rotary sterilization kettles, and the discontinuous sterilization kettles typically comprise discontinuous vertical sterilization kettles and discontinuous horizontal sterilization kettles. Hydrostatic sterilization kettles and discontinuous horizontal sterilization kettles are widely used in China.

Thermal equipment is used for sterilization, and the basic principle is to use high-temperature conditions to kill all kinds of pathogenic bacteria and spoilage bacteria in food, so that the whole sterilization process is basically consistent. The process mainly has three stages.

The first stage is a preheating stage. The food packaging container is in full contact with preheated water in the sterilization kettle, so that the temperature of the packaged food can be increased to gradually approach the sterilization temperature. In addition, the steam consumption and energy consumption can be reduced. The temperature of hot water depends on the type of the used sterilization equipment. If a discontinuous horizontal sterilization kettle is used, hot water with a certain temperature (generally between 50° C. and 90° C.) is usually introduced into the sterilization kettle. If a continuous hydrostatic sterilization equipment is used, the hot water preheating zone is a temperature zone of which the temperature is gradually increased with the decrease of the water column, so that the temperature is closer to the subsequent sterilization temperature.

The second stage is a sterilization stage. After preheating, the packaged food container is sterilized in high-temperature steam or water, and the temperature during this period is generally 100-130° C. Therefore, various pathogenic bacteria and spoilage bacteria are killed.

The third stage is a cooling stage. The cooling stage is arrived after sterilization, so that the food container can make full contact with the cooling water, so that the food temperature is decreased. Based on the different types of the sterilization kettles, there are differences in cooling methods and processes, but the purpose is to reduce the temperature of packaged food. In order to reduce the temperature of the continuous hydrostatic sterilization kettle, the food firstly enters the pressurized cooling zone. The water temperature is relatively high in the cooling zone, and is basically symmetrical with the temperature of the preheating zone. After the food enters the pressurized cooling zone in the machine, the temperature is decreased with the increase of the water column, and then the food enters the atmospheric cooling zone. If a discontinuous horizontal sterilization kettle is used, cooling water is introduced into the sterilization kettle and circulated after sterilization, and the temperature of the sterilization kettle and the packaged food is gradually decreased.

During preheating and cooling, hot water and cold water make full contact with the sterilization kettle body and the packaged food container in the sterilization kettle for corresponding water circulation, and heat is gradually exchanged with the sterilization kettle body and the packaged food to achieve the purposes of preheating and cooling. The sterilization kettle and the packaged food container remain in hot water and cooling water, and the hot water and cooling water can cause serious corrosion to the sterilization kettle body and the packaged food container. In view of the particularity of thermal sterilization production conditions, the sterilization kettle is mainly made of carbon steel, and a few parts are made of stainless steel, copper and other materials. The packaged food container is usually made of glass, tinplate, aluminum alloy, flexible packaging and other materials, and there is a huge galvanic corrosion trend because the sterilization kettle is made of many metal materials. Compared with the traditional open circulating cooling water, the temperature of the hot water and cooling water in the sterilization kettle is much higher, the hot water may be as high as 90° C. or even higher, and the temperature of the cooling water may be as high as 70° C. or even higher, but the high temperature has a higher corrosion tendency. During the cooling process, the residual chlorine content required by the national standard of effluent should be greater than 0.5 ppm, and high residual chlorine can greatly aggravate the metal corrosion.

In view of the particularity of thermal sterilization production, compared with the traditional circulating cooling water, the influence of the corrosion problem on equipment and production is more serious and more difficult to solve. This problem may have a huge impact on thermal sterilization and the appearance of the food container. The serious corrosion leads to frequent maintenance of the equipment, so that the maintenance cost is increased, the productivity is reduced, and the hidden loss caused by shutdown is immeasurable. Corrosion also leads to a significant reduction in the service life of the equipment. The equipment is generally scrapped in about three years in China, or even one year. The sterilization kettle is high-asset equipment with high investment, so that the production cost is virtually increased. The more serious problem is that corrosion products are easily adhered to the surface of the packaged food container, so that the defective rate of packaged food products is greatly increased.

In order to protect the equipment, reduce the maintenance frequency, improve the productivity, increase the finished product rate and reduce the cost, certain chemical treatment needs to be carried out on the water in the process of thermal sterilization to inhibit serious corrosion, and an excellent and complete water treatment control system is important. At present, in the domestic thermal sterilization process, there is basically no complete water treatment system and method because of relatively harsh water treatment conditions and great difficulty.

SUMMARY

The present disclosure aims to provide an automatic control system and method for water treatment of a thermal sterilization kettle. By monitoring some characteristic parameters of preheated water and cooling water in the sterilization kettle, the control for water treatment of the sterilization kettle can be realized, so that the service life of the equipment is prolonged is prolonged for the food production enterprises using the sterilization kettle, the maintenance frequency is reduced, the productivity is improved, the finished product rate is increased, and the cost is reduced.

In order to achieve the-mentioned purpose, the present disclosure provides the following scheme.

Disclosed is an automatic control system for water treatment of a thermal sterilization kettle. The system comprises a sampling module, a monitoring module and a control module, wherein the sampling module comprises a hot sampling pipeline and a cold sampling pipeline, and the hot sampling pipeline and the cold sampling pipeline are respectively used for obtaining sampled hot water from a hot water area and sampled cold water from a cold water area;

the monitoring module comprises a hot water monitoring submodule and a cold water monitoring submodule, the hot water monitoring submodule is used for monitoring the online fluorescence of the sampled hot water, and the cold water monitoring submodule is used for monitoring the online fluorescence and online residual chlorine of the sampled cold water; and the control module comprises a hot water control submodule and a cold water control submodule, the hot water control submodule is connected with the hot water monitoring submodule and used for controlling whether to add a compound medicament into the hot water area according to the online fluorescence signal of the sampled hot water, and the cold water control submodule is connected with the cold water monitoring submodule and used for controlling whether to add the compound medicament into the cold water area according to the online fluorescence signal of the sampled cold water and whether to add an oxidizing bactericide into the cold water area according to the residual chlorine signal of the sampled cold water.

The present disclosure further provides an automatic control method for water treatment of a thermal sterilization kettle, and the method is applied to the control system. The method comprises the following steps:

respectively sampling a hot water area and a cold water area to obtain sampled hot water and sampled cold water;

respectively monitoring the online fluorescence of the sampled hot water and the sampled cold water to obtain the online fluorescence signal of the sampled hot water and the online fluorescence signal of the sampled cold water;

controlling whether to add a compound medicament into the hot water area according to the online fluorescence signal of the sampled hot water, and controlling whether to add the compound medicament into the cold water area according to the online fluorescence signal of the sampled cold water;

carrying out online residual chlorine monitoring on the sampled cold water to obtain the online residual chlorine signal of the sampled cold water; and controlling whether to add an oxidizing bactericide into the cold water area according to the online residual chlorine signal of the sampled cold water.

According to specific embodiments provided by the present disclosure, the present disclosure has the following technical effects.

According to the automatic control system and method for water treatment of a thermal sterilization kettle provided by the present disclosure, the hot sampling pipeline and the cold sampling pipeline are arranged to respectively sample hot water and cold water, and the hot water monitoring submodule and the cold water monitoring submodule are arranged to simultaneously monitor the online fluorescence signals in the sampled hot water and the sampled cold water. Because a certain proportion of fluorescent tracers are compounded in the agent, the online real-time value of agent concentration can be obtained through the intensity of the online fluorescent signals. When the agent concentration value in hot water or cold water is lower than the preset agent concentration threshold, the compound medicament is respectively added into the hot water area through the hot water control submodule and into the cold water area through the cold water control submodule, and the corrosion of the hot water area and the cold water area in the sterilization kettle can be alleviated by adding the compound medicament. Simultaneously, the online residual chlorine of the sampled cold water is monitored through the cold water monitoring submodule. For example, when the online residual chlorine value is lower than the preset residual chlorine threshold, the oxidizing bactericide is added into the cold water area through the cold water control submodule, so that the residual chlorine value in the cold water is higher than the preset residual chlorine threshold, and then the residual chlorine effluent standard is reached. In the scheme of the present disclosure, the hot water and cold water of the sterilization kettle are monitored at the same time, no matter the corrosion of the hot water or the cold water is aggravated or not, the corrosion is relieved by adding the agent, and then the water treatment effect of the sterilization kettle is greatly improved, so that the service life of the sterilization kettle is prolonged, the maintenance frequency is reduced, and the cost is reduced.

BRIEF DESCRIPTION OF THE DRAWINGS

To more clearly illustrate the embodiment of the present disclosure or the technical scheme in the prior art, the following briefly introduces the attached figures to be used in the embodiment. Apparently, the attached figures in the following description show merely some embodiments of the present disclosure, and those skilled in the art may still derive other drawings from these attached figures without creative efforts.

REFERENCE SIGNS 1, sampling module; 2, monitoring module; 3, control module; 4, digital management module; 11, hot sampling pipeline; 12, cold sampling pipeline; 21, hot water monitoring submodule; 22, cold water monitoring submodule; 211, first liquid level sensor; 212, first micro cooler; 213, first temperature detector; 214, second temperature detector; 221, second liquid level sensor; 222, second micro cooler; 223, third temperature detector; 224, fourth temperature detector; 31, hot water control submodule; and 32, cold water control submodule.

DETAILED DESCRIPTION OF THE EMBODIMENTS

The following clearly and completely describes the technical scheme in the embodiments of the present disclosure with reference to the attached figures in the embodiments of the present disclosure. Apparently, the described embodiments are merely a part rather than all of the embodiments of the present disclosure. Based on the embodiment in the present disclosure, all other embodiments obtained by the ordinary technical staff in the art under the premise of without contributing creative labor belong to the scope protected by the present disclosure.

The present disclosure aims to provide an automatic control system and method for water treatment of a thermal sterilization kettle. The hot water and cold water in the sterilization kettle are monitored and controlled at the same time, the water treatment effect of the sterilization kettle can be greatly improved, the service life of the equipment is prolonged is prolonged for the food production enterprises using the sterilization kettle, the maintenance frequency is reduced, the production continuity and production efficiency are improved, the finished product rate is increased, the cost is reduced, and the competitiveness of the enterprises is enhanced.

To make the foregoing objective, features and advantages of the present disclosure clearer and more comprehensible, the present disclosure is further described in detail below with reference to the attached figures and specific embodiments.

Embodiment I

Figure 1:
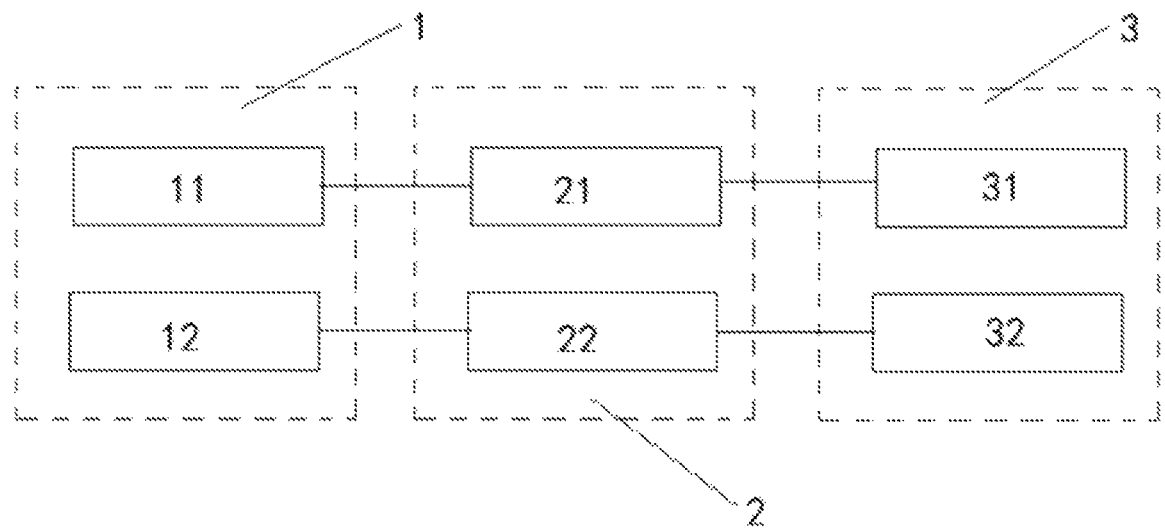
FIG. 1 is a structure diagram of an automatic control system for water treatment of a thermal sterilization kettle provided by the first embodiment of the present disclosure.

The embodiment provides an automatic control system for water treatment of a thermal sterilization kettle, referring to FIG. 1. The system comprises a sampling module 1, a monitoring module 2 and a control module 3.

The sampling module 1 comprises a hot sampling pipeline 11 and a cold sampling pipeline 12. The hot sampling pipeline 11 and the cold sampling pipeline 12 are respectively used for obtaining sampled hot water from a hot water area and sampled cold water from a cold water area.

The monitoring module 2 comprises a hot water monitoring submodule 21 and a cold water monitoring submodule 22. The hot water monitoring submodule 21 is used for monitoring the online fluorescence of the sampled hot water. The cold water monitoring submodule 22 is used for monitoring the online fluorescence and online residual chlorine of the sampled cold water.

It should be noted that, in the embodiment, sensors can be arranged correspondingly according to the information to be monitored. For example, if the online fluorescence of the sampled water is monitored, the hot water monitoring submodule 21 and the cold water monitoring submodule 22 both comprise online fluorescence sensors, and if the online residual chlorine of the sampled cold water needs to be monitored, the cold water monitoring submodule 22 further comprises an online residual chlorine sensor.

The control module 3 comprises a hot water control submodule 31 and a cold water control submodule 32. The hot water control submodule 31 is connected with the hot water monitoring submodule 21 and used for controlling whether to add a compound medicament into the hot water area according to the online fluorescence signal of the sampled hot water. The cold water control submodule 32 is connected with the cold water monitoring submodule 22 and used for controlling whether to add the compound medicament into the cold water area according to the online fluorescence signal of the sampled cold water.

The compound medicament comprises a dispersant, a corrosion inhibitor, a scale inhibitor and other agents. By compounding a certain proportion of fluorescent tracers in the used agent, and the fluorescence intensity is monitored through the online fluorescence sensor to obtain the online real-time value of agent concentration. The agent is added by setting the control range of the agent concentration. If the agent concentration is controlled at 10±1 ppm, a dosing pump is turned on for dosing through the control module 3 when the agent concentration is lower than 9 ppm, and then the dosing pump is turned off to stop dosing through the control module 3 when the concentration is detected to be higher than 11 ppm.

In actual, the temperature of preheated water and cooling water in the sterilization kettle often exceeds 50° C., resulting in challenges to the monitoring of the agent concentration. At a relatively high temperature, the monitoring of the fluorescence signal may be deviated and the detection is no longer accurate, resulting in great challenges to the control of water treatment and influence on the water treatment effect to some extent.

As an optional implementation method, in the embodiment, the hot water monitoring submodule 21 further comprises a first micro cooler 212, a first temperature detector 213 and a second temperature detector 214. The first micro cooler 212 is arranged on the hot sampling pipeline 11. The first temperature detector 213 and the second temperature detector 214 are respectively arranged in front of and at the back of the first micro cooler 212 and respectively used for detecting the temperature of water before entering the first micro cooler 212 and after passing through the first micro cooler 212. The hot water control submodule 31 is further used for controlling the start and stop of the first micro cooler 212 according to the temperature of water detected by the first temperature detector 213.

The cold water monitoring submodule 22 further comprises a second micro cooler 222, a third temperature detector 223 and a fourth temperature detector 224. The second micro cooler 222 is arranged on the cold sampling pipeline 12. The third temperature detector 223 and the fourth temperature detector 224 are respectively arranged in front of and at the back of the second micro cooler 222 and respectively used for detecting the temperature of water before entering the second micro cooler 222 and after passing through the second micro cooler 222. The cold water control submodule 32 is further used for controlling the start and stop of the second micro cooler 222 according to the temperature of water detected by the third temperature detector 223.

The micro coolers are respectively installed in the water sampling pipelines of hot water and cooling water, so that the temperature of water entering the online fluorescence sensor is lower than 45° C., and the detection accuracy of the online fluorescence signal is improved. Temperature sensors are installed in front of and at the back of the cooler to control the start and stop of the cold water of the micro cooler through temperature signals.

In the existing water treatment, a large amount of oxidizing bactericide is mostly added into the cooling water according to the requirements of national standards to reach the effluent residual chlorine standard of more than 0.5 ppm. However, the residual chlorine signal is basically detected manually at a fixed time, and then the oxidizing bactericide is added into the cooling water manually or continuously through a timer, usually resulting in that the residual chlorine value of the cooling water is much higher than 0.5 ppm for a long time and the corrosion problem is extremely serious.

In the embodiment, the cold water monitoring submodule 22 further monitors the online residual chlorine (or oxidation reduction potential ORP) of the sampled cold water, and the cold water control submodule 32 is further used for controlling whether to add the oxidizing bactericide into the cold water area according to the residual chlorine signal (or oxidation reduction potential ORP) of the sampled cold water. If the control range of the residual chlorine is 0.6±0.1 ppm, the dosing pump is turned on through the cold water control submodule 32 to add the oxidizing bactericide when the residual chlorine is lower than 0.5 ppm, and then the dosing pump is turned off through the cold water control submodule 32 to stop adding the oxidizing bactericide when the residual chlorine is higher than 0.7 ppm, so that the residual chlorine value of the cooling water can be accurately controlled to be more than 0.5 ppm so as to meet the standard, but less than 0.7 ppm at the same time so as to minimize the influence of the residual chlorine on corrosion. Whether to add the oxidizing bactericide can be controlled through the ORP signal. The residual chlorine value has a certain corresponding value to the oxidation reduction potential, and the value depends on the water quality of each site. Firstly, the corresponding relationship is determined. If it is determined that the residual chlorine of certain water is 0.5 ppm, the corresponding ORP value is 500 mV, and then the ORP range can be set to be 550±50 mV. When the corresponding ORP value is lower than 500 mV, the addition of the oxidizing bactericide is controlled. When the corresponding ORP value is higher than 600 mV, the addition of the oxidizing bactericide is stopped.

The hot water and cold water in the sterilization kettle can not only cause corrosion hazards to the kettle metal and packaged food containers but also easily cause scaling, deposition, microbial fouling and other hazards. In the production process, some parts need to be coated with lubricating oil so as to enhance the lubricity of connecting or rotating parts, but the lubricating oil can breed microbial problems, so that the water body has a huge trend in microbial breeding, and dirt is easily formed. At the same time, the phenomenon of can explosion may occur in the production process. Food leaks into the water from the container, so that the organic content in the water is increased, the breeding and reproduction of microorganisms are promoted, and dirt is easily formed. Besides the reduction of heat exchange efficiency, the influence of scaling, deposition, microbial fouling mainly affects the food container. Once scaling and fouling are deposited on the outer surface of the food container, the food safety is seriously affected, and the finished product rate is reduced. Therefore, it is also very important to solve scaling, deposition and microbial contamination to ensure the food safety and equipment protection, improve the productivity and reduce the cost.

Above all, in the embodiment, the hot water monitoring submodule 21 is further used for monitoring the conductivity, total iron, turbidity and chemical oxygen demand of the sampled hot water, and the hot water control submodule 31 is further used for controlling the hot water blowdown in the hot water area according to the conductivity, total iron, turbidity and chemical oxygen demand signals of the sampled hot water.

The cold water monitoring submodule 22 is further used for monitoring the conductivity, total iron, turbidity and chemical oxygen demand of the sampled cold water. The cold water control submodule 32 is further used for controlling the cold water blowdown in the cold water area according to the conductivity, total iron, turbidity and chemical oxygen demand signals of the sampled cold water.

Generally, in the embodiment, the blowdown is controlled by using the set range of the conductivity. If the conductivity is controlled to be 500±20 μs/cm, when the conductivity is higher than 520 μs/cm, a blowdown pump is turned on for blowdown through the control module 3 until the conductivity is lower than 480 μs/cm, and then the blowdown pump is turned off to stop blowdown through the control module 3.

The specific situation of the hot water and cooling water in the sterilization kettle is slightly different from that of traditional open circulating cooling water, and has the particularities such as high total iron, high residual chlorine and high COD (chemical oxygen demand) These parameters cannot be reflected in the traditional circulating cooling water control system, and the blowdown of hot water and cooling water cannot be completely carried out according to the traditional conductivity setting range mode.

Through the scheme provided by the embodiment, when hot water and cooling water encounter harsh water-quality environment, blowdown can also be carried out. For example, when corrosion is deteriorated, the content of total iron, turbidity or online COD exceeds the critical value, the blowdown pump can be turned on through the control module 3 for blowdown forcibly until the corresponding value reaches a reasonable range. For example, if the tolerable total iron range is 0.5-2 ppm, when the total iron is greater than 2 ppm, the blowdown pump can be turned on for blowdown forcibly until the total iron is less than 0.5 ppm, and then the blowdown pump is turned off to stop blowdown even if the conductivity of the hot water system does not reach the blowdown standard.

It needs to be noted that, for those skilled in the art, the monitoring module 2 is provided with other corresponding sensors according to the needs. For example, when the pH values of the hot water area and the cold water area need to be monitored, the hot water monitoring submodule 21 and the cold water monitoring submodule 22 are provided with pH sensors, so that the pH values of the water in the hot sampling pipeline 11 and the cold sampling pipeline 12 are respectively monitored. When the corrosion rates of the hot water area and the cold water area need to be monitored, the hot water monitoring submodule 21 and the cold water monitoring submodule 22 are provided with online corrosion rate sensors or corrosion coupon, so that the corrosion conditions in the hot sampling pipeline 11 and the cold sampling pipeline 12 re respectively monitored. The embodiment is not limited to this.

The total iron, COD and turbidity in the hot water or cold water are effectively reduced through blowdown, but the water level in the hot water area or cold water area can be reduced as well. Above all, in the embodiment, the hot water monitoring submodule 21 comprises a first liquid level sensor 211, and the first liquid level sensor 211 is arranged in the hot water area and used for acquiring the liquid level signal of the hot water area; and the cold water monitoring submodule 22 comprises a second liquid level sensor 221, and the second liquid level sensor 221 is arranged in the cold water area and used for acquiring the liquid level signal of the cold water area.

The hot water control submodule 31 is further used for controlling water supply to the hot water area according to the liquid level signal of the hot water area, and the cold water control submodule 32 is further used for controlling water supply to the cold water area according to the liquid level signal of the cold water area.

In consideration of the problem of data recording in the water treatment process of the sterilization kettle and the digital management for users, the water treatment efficiency of the sterilization kettle is improved. The control system for water treatment provided by the embodiment further comprises a digital management module 4. The digital management module 4 is connected with the sampling module 1, the monitoring module 2 and the control module 3 and used for recording the data of each module of the system and storing the data in the cloud.

Embodiment II

Figure 2:
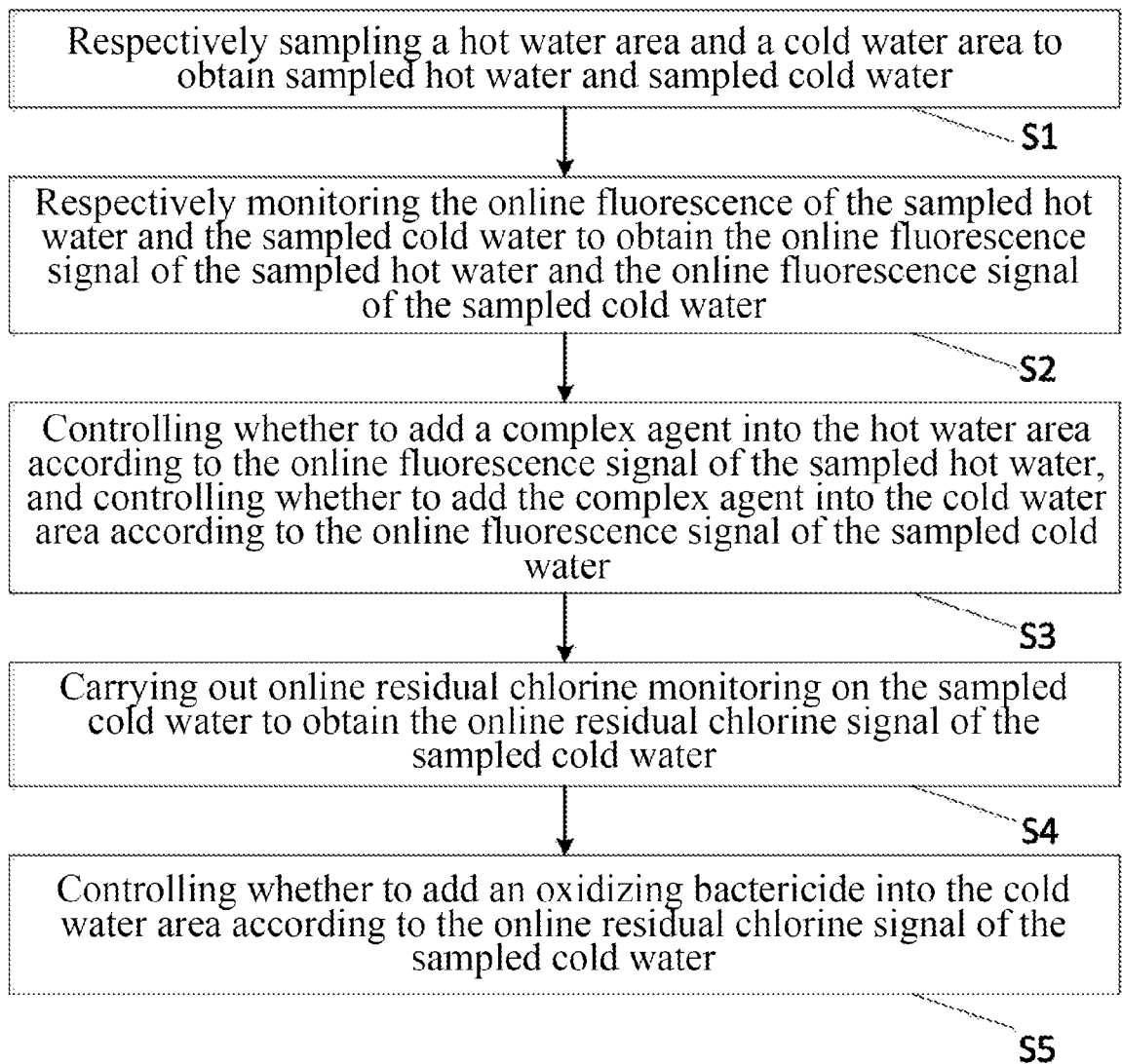
FIG. 2 is a flow diagram of an automatic control method for water treatment of a thermal sterilization kettle provided by the second embodiment of the present disclosure.

The embodiment provides an automatic control system for water treatment of a thermal sterilization kettle. The method provided by the embodiment is applied to the system in the first embodiment, referring to FIG. 2. The method comprises the following steps:
respectively sampling a hot water area and a cold water area to obtain sampled hot water and sampled cold water;
respectively monitoring the online fluorescence of the sampled hot water and the sampled cold water to obtain the online fluorescence signal of the sampled hot water and the online fluorescence signal of the sampled cold water;
controlling whether to add a compound medicament into the hot water area according to the online fluorescence signal of the sampled hot water, and controlling whether to add the compound medicament into the cold water area according to the online fluorescence signal of the sampled cold water;
carrying out online residual chlorine monitoring on the sampled cold water to obtain the online residual chlorine signal of the sampled cold water; and
controlling whether to add an oxidizing bactericide into the cold water area according to the online residual chlorine signal of the sampled cold water.

As an optional implementation method, the method further comprises the following steps:
respectively monitoring the conductivity, total iron, turbidity and chemical oxygen demand of the sampled hot water and the sampled cold water;
controlling whether to carry out blowdown on the cold water in the cold water area according to the conductivity, total iron, turbidity and chemical oxygen demand signals of the sampled cold water; and
controlling whether to carry out blowdown on the hot water in the hot water area according to the conductivity, total iron, turbidity and chemical oxygen demand signals of the sampled hot water.

As an optional implementation method, the method further comprises the following steps:
acquiring the liquid level signal of the hot water area through a first liquid level sensor 211, and acquiring the liquid level signal of the cold water area through a second liquid level sensor 221; and
controlling water supply to the hot water area according to the liquid level signal of the hot water area, and controlling water supply to the cold water area according to the liquid level signal of the cold water area.

Optionally, a first micro cooler is arranged on a hot sampling pipeline, and a second micro cooler is arranged on a cold sampling pipeline. The method further comprises the following steps:
monitoring the temperature of water before entering the first micro cooler 212 by using a first temperature detector 213, and monitoring the temperature of water after passing through the first micro cooler 212 by a second temperature detector 214;
controlling the start and stop of the first micro cooler 212 according to the temperature of water monitored by the first temperature detector 213 and the temperature of water monitored by the second temperature detector 214;
monitoring the temperature of water before entering the second micro cooler 222 by using a third temperature detector 223, and monitoring the temperature of water after passing through the second micro cooler 222 by a fourth temperature detector 224; and
controlling the start and stop of the second micro cooler 222 according to the temperature of water monitored by the third temperature detector 223 and the temperature of water monitored by the fourth temperature detector 224.

As an optional implementation method, the method further comprises the following steps:
recording the data in the automatic control process of water treatment of the sterilization kettle through a digital module 4, and storing the data in the cloud.

According to the automatic control system and method for water treatment of a thermal sterilization kettle provided by the present disclosure, accurate monitoring of the hot water and cooling water of the sterilization kettle can be provided at the same time, the water treatment effect of the sterilization kettle is greatly improved, the service life of the sterilization kettle is prolonged, the maintenance frequency is reduced, the productivity is improved, the cost is reduced, and the competitiveness of enterprises is enhanced.

By introducing more water quality treatment result window parameters such as total iron, corrosion rate, turbidity and COD, the blowdown mode is regulated and controlled possibly based on the result orientation (such as total iron, turbidity and online COD), so that the disadvantages (such as various corrosion and fouling deposition caused by high total iron, turbidity and COD) caused by single conductivity control are avoided, and the water treatment effect is improved.

The micro coolers are installed in sampled water of hot water and cooling water, and accurate detection of the online fluorescence signal at high temperature can be realized, so that the monitoring of the agent concentration is more accurate, and the water treatment effect is better.

The water treatment efficiency of the sterilization kettle is improved through digital management.

All embodiments in this specification are described in a progressive manner. Each embodiment focuses on differences from other embodiments. For the part that is the same or similar between different embodiments, reference may be made between the embodiments.

Several examples are used for illustration of the principles and implementation methods of the present disclosure. The description of the embodiments is used to help illustrate the method and the core principles of the present disclosure; and meanwhile, those skilled in the art can make various modifications in terms of specific embodiments and scope of application in accordance with the teachings of the present disclosure. In conclusion, the content of this specification shall not be construed as a limitation to the present disclosure.

What is claimed is:

1. An automatic control system for water treatment of a thermal sterilization kettle, comprising a sampling module, a monitoring module and a control module, wherein
the sampling module comprises a hot sampling pipeline and a cold sampling pipeline, wherein the hot sampling pipeline is connected with a hot water area of the thermal sterilization kettle and the cold sampling pipeline is connected with a cold water area of the thermal sterilization kettle, the hot sampling pipeline is configured to obtain sampled hot water from the hot water area of the thermal sterilization kettle and the cold sampling pipeline is configured to obtain sampled cold water from the cold water area of thermal sterilization kettle;
the monitoring module comprises a hot water monitoring submodule and a cold water monitoring submodule, wherein the hot water monitoring submodule is connected with the hot sampling pipeline and configured to monitor online fluorescence of the sampled hot water, and the cold water monitoring submodule is connected with the cold sampling pipeline and configured to monitor online fluorescence and online residual chlorine of the sampled cold water;
the control module comprises a hot water control submodule and a cold water control submodule, wherein the hot water control submodule is connected with the hot water monitoring submodule and configured to control whether to add a compound medicament into the hot water area according to an online fluorescence signal of the sampled hot water output from the hot water monitoring submodule; and the cold water control submodule is connected with the cold water monitoring submodule and configured to control whether to add the compound medicament into the cold water area according to an online fluorescence signal of the sampled cold water output from the cold water monitoring submodule and whether to add an oxidizing bactericide into the cold water area according to an online residual chlorine signal of the sampled cold water output from the cold water monitoring submodule;
wherein
the hot water monitoring submodule further comprises a first micro cooler, a first temperature detector and a second temperature detector, wherein the first micro cooler is arranged on the hot sampling pipeline, the first temperature detector and the second temperature detector are respectively arranged in front of and at the back of the first micro cooler, the first temperature detector is configured to detect a temperature of water before entering the first micro cooler and the second temperature detector is configured to detect a temperature of water after passing through the first micro cooler, and the hot water control submodule is further configured to control start or stop of the first micro cooler according to the temperature of water detected by the first temperature detector; and
the cold water monitoring submodule further comprises a second micro cooler, a third temperature detector and a fourth temperature detector, wherein the second micro cooler is arranged on the cold sampling pipeline, the third temperature detector and the fourth temperature detector are respectively arranged in front of and at the back of the second micro cooler, the third temperature detector is configured to detect a temperature of water before entering the second micro cooler and the fourth temperature detector is configured to detect a temperature of water after passing through the second micro cooler, and the cold water control submodule is further configured to control start or stop of the second micro cooler according to the temperature of water detected by the third temperature detector.

2. The system according to claim 1, wherein the hot water monitoring submodule is further configured to monitor conductivity, total iron, turbidity and chemical oxygen demand of the sampled hot water, and the hot water control submodule is further configured to control hot water blowdown in the hot water area according to the conductivity, total iron, turbidity and chemical oxygen demand of the sampled hot water; and
the cold water monitoring submodule is further configured to monitor conductivity, total iron, turbidity and chemical oxygen demand of the sampled cold water, and the cold water control submodule is further configured to control cold water blowdown in the cold water area according to the conductivity, total iron, turbidity and chemical oxygen demand of the sampled cold water.

3. The system according to claim 2, wherein the hot water monitoring submodule comprises a first liquid level sensor, wherein the first liquid level sensor is arranged in the hot water area and configured to acquire a liquid level signal of the hot water area; and the cold water monitoring submodule comprises a second liquid level sensor, wherein the second liquid level sensor is arranged in the cold water area and configured to acquire a liquid level signal of the cold water area; and
the hot water control submodule is further configured to control water supply to the hot water area according to the liquid level signal of the hot water area, and the cold water control submodule is further configured to control water supply to the cold water area according to the liquid level signal of the cold water area.

4. The system according to claim 1, further comprising a digital management module, wherein the digital management module is connected with the sampling module, the monitoring module and the control module, and the digital management module is configured to record data output by the sampling module, the monitoring module and the control module, and store the data in a cloud.

5. An automatic control method for water treatment of the thermal sterilization kettle, applied to the system according to claim 1, comprising the following steps:

respectively sampling the hot water area and the cold water area to obtain the sampled hot water and the sampled cold water;

respectively monitoring the online fluorescence of the sampled hot water and the sampled cold water to obtain the online fluorescence signal of the sampled hot water and the online fluorescence signal of the sampled cold water;

controlling whether to add the compound medicament into the hot water area according to the online fluorescence signal of the sampled hot water, and controlling whether to add the compound medicament into the cold water area according to the online fluorescence signal of the sampled cold water;

carrying out online residual chlorine monitoring on the sampled cold water to obtain the online residual chlorine signal of the sampled cold water; and controlling whether to add the oxidizing bactericide into the cold water area according to the online residual chlorine signal of the sampled cold water.

6. The method according to claim 5, wherein the hot water monitoring submodule is further configured to monitor conductivity, total iron, turbidity and chemical oxygen demand of the sampled hot water, and the hot water control submodule is further configured to:

control hot water blowdown in the hot water area according to the conductivity, total iron, turbidity and chemical oxygen demand of the sampled hot water; and the cold water monitoring submodule is further configured to monitor conductivity, total iron, turbidity and chemical oxygen demand of the sampled cold water, and the cold water control submodule is further configured to control cold water blowdown in the cold water area according to the conductivity, total iron, turbidity and chemical oxygen demand of the sampled cold water.

7. The method according to claim 6, wherein the hot water monitoring submodule comprises a first liquid level sensor, wherein the first liquid level sensor is arranged in the hot water area and configured to acquire a liquid level signal of the hot water area;

the cold water monitoring submodule comprises a second liquid level sensor, wherein the second liquid level sensor is arranged in the cold water area and configured to acquire a liquid level signal of the cold water area; and the hot water control submodule is further configured to control water supply to the hot water area according to the liquid level signal of the hot water area, and the cold water control submodule is further configured to control water supply to the cold water area according to the liquid level signal of the cold water area.

8. The method according to claim 5, further comprising a digital management module, wherein the digital management module is connected with the sampling module, the monitoring module and the control module, and the digital management module is configured to record data output by the sampling module, the monitoring module and the control module, and store the data in a cloud.

9. The method according to claim 5, further comprising the following steps:

respectively monitoring conductivity, total iron, turbidity and chemical oxygen demand of the sampled hot water and the sampled cold water;

controlling whether to carry out cold water blowdown in the cold water area according to the conductivity, total iron, turbidity and chemical oxygen demand of the sampled cold water; and controlling whether to carry out hot water blowdown in the hot water area according to the conductivity, total iron, turbidity and chemical oxygen demand of the sampled hot water.

10. The method according to claim 6, further comprising the following steps:

respectively monitoring the conductivity, total iron, turbidity and chemical oxygen demand of the sampled hot water and the sampled cold water;

controlling whether to carry out the cold water blowdown in the cold water area according to the conductivity, total iron, turbidity and chemical oxygen demand of the sampled cold water; and controlling whether to carry out the hot water blowdown in the hot water area according to the conductivity, total iron, turbidity and chemical oxygen demand of the sampled hot water.

11. The method according to claim 7, further comprising the following steps:

respectively monitoring the conductivity, total iron, turbidity and chemical oxygen demand of the sampled hot water and the sampled cold water;

controlling whether to carry out the cold water blowdown in the cold water area according to the conductivity, total iron, turbidity and chemical oxygen demand of the sampled cold water; and controlling whether to carry out the hot water blowdown in the hot water area according to the conductivity, total iron, turbidity and chemical oxygen demand of the sampled hot water.

12. The method according to claim 8, further comprising the following steps:

respectively monitoring conductivity, total iron, turbidity and chemical oxygen demand of the sampled hot water and the sampled cold water;

controlling whether to carry out cold water blowdown in the cold water area according to the conductivity, total iron, turbidity and chemical oxygen demand of the sampled cold water; and controlling whether to carry out hot water blowdown in the hot water area according to the conductivity, total iron, turbidity and chemical oxygen demand of the sampled hot water.

13. The method according to claim 9, further comprising the following steps:

acquiring a liquid level signal of the hot water area through a first liquid level sensor, and acquiring a liquid level signal of the cold water area through a second liquid level sensor; and controlling water supply to the hot water area according to the liquid level signal of the hot water area, and controlling water supply to the cold water area according to the liquid level signal of the cold water area.

14. The method according to claim 10, further comprising the following steps:

acquiring a liquid level signal of the hot water area through a first liquid level sensor, and acquiring a liquid level signal of the cold water area through a second liquid level sensor; and controlling water supply to the hot water area according to the liquid level signal of the hot water area, and controlling water supply to the cold water area according to the liquid level signal of the cold water area.

15. The method according to claim 11, further comprising the following steps:
- acquiring the liquid level signal of the hot water area through the first liquid level sensor, and acquiring the liquid level signal of the cold water area through the second liquid level sensor; and
- controlling the water supply to the hot water area according to the liquid level signal of the hot water area, and controlling the water supply to the cold water area according to the liquid level signal of the cold water area.

16. The method according to claim 12, further comprising the following steps:
- acquiring a liquid level signal of the hot water area through a first liquid level sensor, and acquiring a liquid level signal of the cold water area through a second liquid level sensor; and
- controlling water supply to the hot water area according to the liquid level signal of the hot water area, and controlling water supply to the cold water area according to the liquid level signal of the cold water area.

17. The method according to claim 5, wherein a first micro cooler is arranged on a hot sampling pipeline, and a second micro cooler is arranged on a cold sampling pipeline; the method further comprises the following steps:
- monitoring a temperature of water before entering the first micro cooler by using a first temperature detector, and monitoring a temperature of water after passing through the first micro cooler by a second temperature detector;
- controlling start or stop of the first micro cooler according to the temperature of water monitored by the first temperature detector and the temperature of water monitored by the second temperature detector;
- monitoring a temperature of water before entering the second micro cooler by using a third temperature detector, and monitoring a temperature of water after passing through the second micro cooler by a fourth temperature detector; and
- controlling start or stop of the second micro cooler according to the temperature of water monitored by the third temperature detector and the temperature of water monitored by the fourth temperature detector.

18. The method according to claim 6, wherein a first micro cooler is arranged on a hot sampling pipeline, and a second micro cooler is arranged on a cold sampling pipeline; the method further comprises the following steps:
- monitoring a temperature of water before entering the first micro cooler by using a first temperature detector, and monitoring a temperature of water after passing through the first micro cooler by a second temperature detector;
- controlling start or stop of the first micro cooler according to the temperature of water monitored by the first temperature detector and the temperature of water monitored by the second temperature detector;
- monitoring a temperature of water before entering the second micro cooler by using a third temperature detector, and monitoring a temperature of water after passing through the second micro cooler by a fourth temperature detector; and
- controlling start or stop of the second micro cooler according to the temperature of water monitored by the third temperature detector and the temperature of water monitored by the fourth temperature detector.

19. The method according to claim 7, wherein a first micro cooler is arranged on a hot sampling pipeline, and a second micro cooler is arranged on a cold sampling pipeline; the method further comprises the following steps:
- monitoring a temperature of water before entering the first micro cooler by using a first temperature detector, and monitoring a temperature of water after passing through the first micro cooler by a second temperature detector;
- controlling start or stop of the first micro cooler according to the temperature of water monitored by the first temperature detector and the temperature of water monitored by the second temperature detector;
- monitoring a temperature of water before entering the second micro cooler by using a third temperature detector, and monitoring a temperature of water after passing through the second micro cooler by a fourth temperature detector; and
- controlling start or stop of the second micro cooler according to the temperature of water monitored by the third temperature detector and the temperature of water monitored by the fourth temperature detector.

20. The method according to claim 5, further comprising the following step:
- recording generated data during the method of claim 5 through a digital module, and storing the data in a cloud.

* * * * *